United States Patent [19]

Moseley

[11] Patent Number: 4,460,356
[45] Date of Patent: Jul. 17, 1984

[54] CATHETER ANCHOR TAPE

[76] Inventor: Douglas Moseley, 845 Ludlow - E-203, Rochester, Mich. 48063

[21] Appl. No.: 347,405

[22] Filed: Feb. 10, 1982

[51] Int. Cl.³ ............................................ A61M 25/02
[52] U.S. Cl. .................................................. 604/180
[58] Field of Search .............................. 604/180, 174; 128/DIG. 26, 133; 248/205 A; 24/DIG. 11

[56] References Cited

U.S. PATENT DOCUMENTS

| | | | |
|---|---|---|---|
| 2,821,194 | 1/1958 | Simmons | 604/180 |
| 3,422,817 | 1/1969 | Mishkin et al. | 128/351 |
| 3,677,250 | 7/1972 | Thomas | 604/180 |
| 3,826,254 | 7/1974 | Mellor | 128/DIG. 26 |
| 3,927,676 | 12/1975 | Schultz | 128/351 |
| 4,057,066 | 11/1977 | Taylor | 128/349 R |
| 4,074,397 | 2/1978 | Rosin | 128/DIG. 26 |
| 4,221,215 | 9/1980 | Mandelbaum | 128/155 |

Primary Examiner—C. Fred Rosenbaum
Assistant Examiner—Sherri E. Vinyard
Attorney, Agent, or Firm—Reising, Ethington, Barnard, Perry & Milton

[57] ABSTRACT

A pre-cut anchor tape is disclosed for securing an intravenous catheter to the arm of a person. A unitary strip of tape is slit to form three interconnected longitudinally extending bands, the bands being connected by an uncut portion near the mid-length of the strip. One of the side bands has an adhesive on its inner surface for adhering the tape to the person's arm. The intermediate band has an adhesive on its upper surface so that its free ends may be wrapped half-way around the catheter and adhered thereto and to the person's arm. The other side band has an adhesive on either its inner or outer surface and is used for additional securement of the catheter to the arm.

4 Claims, 8 Drawing Figures

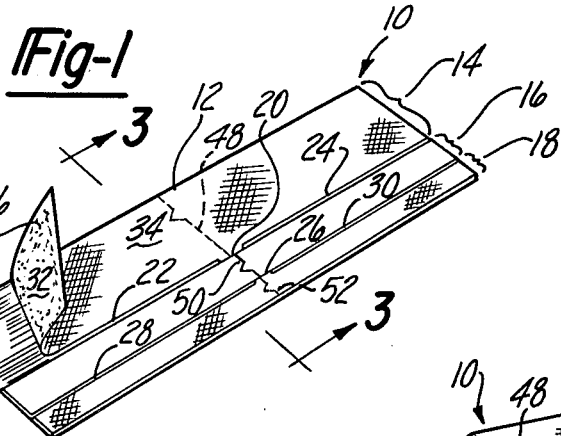
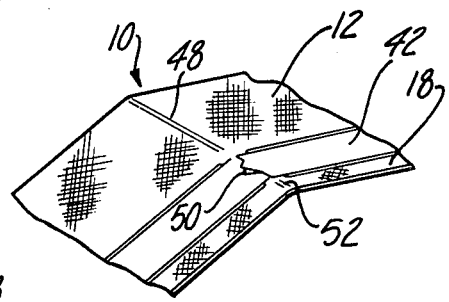
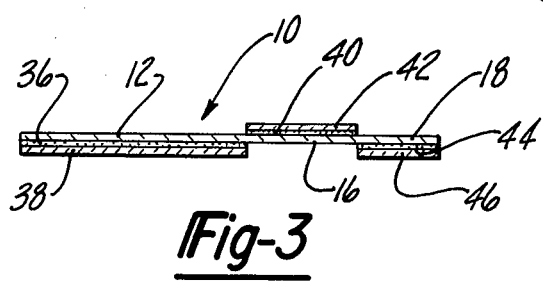
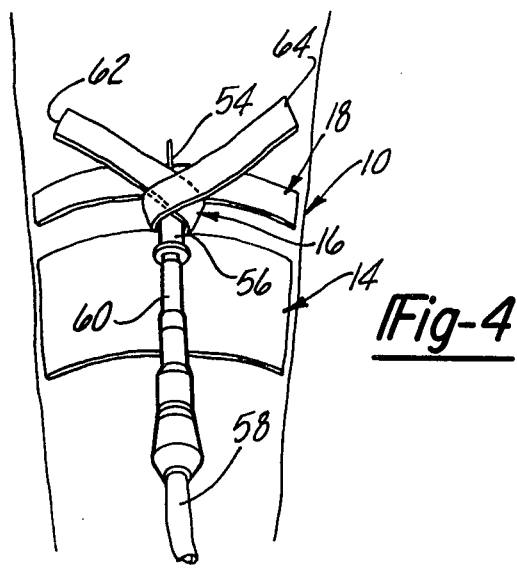

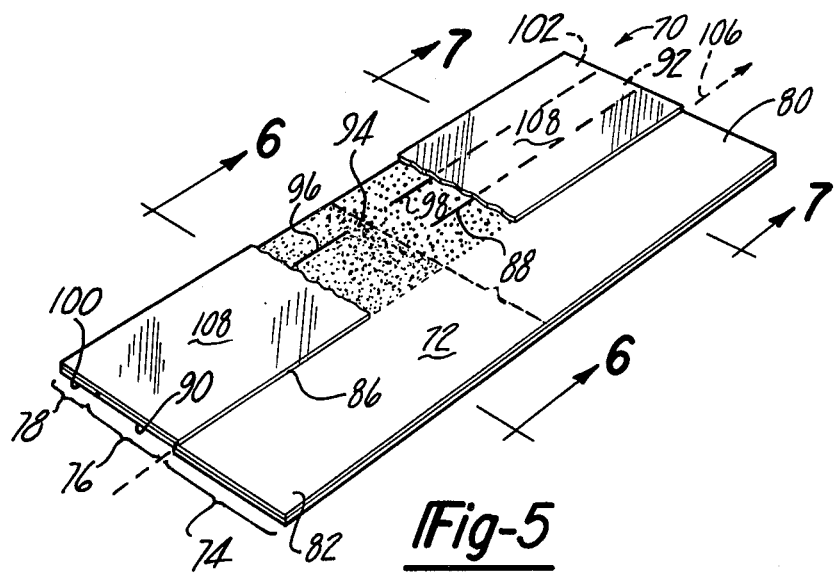
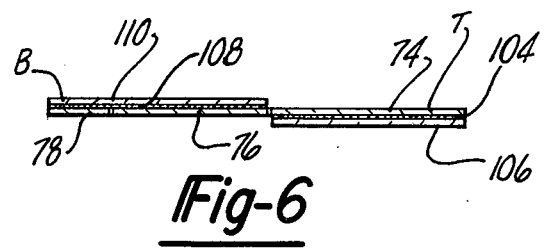
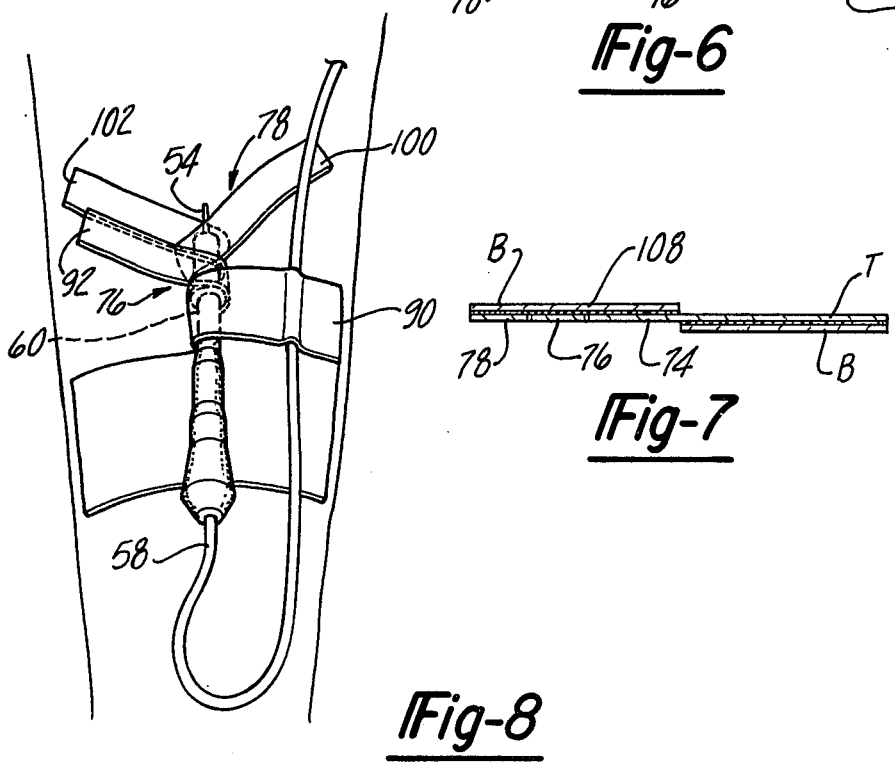

4,460,356

CATHETER ANCHOR TAPE

FIELD OF THE INVENTION

This invention relates to surgical catheters and more particularly to an anchor tape for securing a catheter or the like to the patient to prevent undesired dislocation of the catheter.

BACKGROUND ART

In administering emergency medical aid, it is frequently necessary to use an intravenous (IV) catheter to supply the patient with needed body fluid or medication. Most commonly the IV catheter is inserted into the arm. This is frequently done by a paramedic or a nurse under adverse conditions. It is also done routinely in a hospital. Whatever the circumstances, there is a great need for an improved device for anchoring an IV catheter to the patient so that it will not be dislocated accidentally.

Heretofore, it has been common practice for the paramedic or nurse to make an anchor tape by applying individual strips of tape to hold the catheter in place. A common practice is to cut five strips of tape; two strips are separately wrapped once around the catheter and the free ends are stuck to the arm. The remaining three strips are applied as needed to help hold the catheter in place. Applying such a device is sometimes awkward and time consuming, especially under adverse conditions of an emergency, and frequently the catheter is not secured as it should be.

No devices for securing an IV catheter to a patient's body, other than the individual tape strips described above, are known to me at the present time. A patent search on the subject invention revealed the following patents:

Mishkin et al U.S. Pat. No. 3,422,817 discloses a tracheometry bandage comprising a resilient frame with a covering shaped to provide a central opening with overlapping end portions. The frame can be moved to separate the overlapping portion for application and removal of the bandage from the tracheometry tube. The bandage grips the tube when in use.

Schultz U.S. Pat. No. 3,927,676 discloses an endotracheal tube securing device comprising a length of flexible tape having a non-adhesive central portion with bifurcated ends which are adhesively coated on one side. The device is applied by looping the central portion under the neck of the patient, drawing the bifurcated ends across the patient's cheeks and successively wrapping the free ends around the tube to secure it against movement.

Taylor U.S. Pat. No. 4,057,066 discloses an urethral catheter holder comprising an adhesive anchoring strip with a cord passing through openings therein and tied thereto to secure it in place. The cord is looped around the connector of the catheter and tied to secure the catheter against movement.

Rosin U.S. Pat. No. 4,074,397 discloses a device for securing cords, tubes and the like during surgical operations. It comprises a thin flexible pad adhesively attached to the bed sheet or bed-rail with an elongated flexible strip extending from the pad for wrapping around the tube to be secured. The free end of the strip is attached to the pad itself by a pressure sensitive fastener.

Mandelbaum U.S. Pat. No. 4,221,215 discloses a surgical dressing which is used to anchor a medical device, such as a chest tube. The dressing includes an opening with elongated bands adjacent thereto to connect the medical device to the dressing. That portion of the dressing with the opening has an adhesive on the rear surface for attaching the dressing to the patient. The other portion of the dressing has adhesive on the front surface so that it can be folded over and adhesively attached to the first portion after removal of the medical device to occlude the cut made in the patient.

A general object of this invention is to provide a catheter anchor tape which overcomes the disadvantages of the prior art devices.

SUMMARY OF THE INVENTION

In accordance with this invention, a catheter anchor tape is provided which is quickly and easily applied to the patient and which is highly effective in securing the catheter against dislocation. This is accomplished by a pre-cut strip of tape having a first side band provided with an adhesive on the inner surface of the tape and adapted to be adhesively attached to the patient throughout the length of the band. An intermediate band on the strip of tape is unitarily joined to the first band only by a unitary junction near the mid-length of the strip and a second side band is unitarily joined with the intermediate band only by a unitary junction near the mid-length of the strip. The intermediate band is provided with an adhesive on the outer surface and the free ends thereof are adapted to be wrapped half-way around the catheter and adhered thereto and to the skin of the patient. The second side band is, in one embodiment, provided with an adhesive on the upper surface and the free ends are adapted to be wrapped half-way around the catheter and adhered thereto and to the skin of the patient. In another embodiment, the second side band is provided with an adhesive on the inner surface and the free ends are adhered to the skin of the patient throughout the length thereof. In the first embodiment, it is preferred to make one of the free ends of the intermediate band wider than the other. In this construction, the wider free end overlaps the first side band and the skin of the patient. This arrangement is especially adapted to provide a hold-down for the tubing extending to the catheter.

A more complete understanding of this invention may be obtained from the detailed description that follows taken with the accompanying drawings.

DESCRIPTION OF THE DRAWINGS

FIG. 1 is a perspective view of one embodiment of the anchor tape of this invention;

FIG. 2 shows the tape in position for facilitating removal of the backing strip from the adhesive;

FIG. 3 shows a section taken on line 3—3 of FIG. 1;

FIG. 4 is a perspective view showing the anchor tape applied to a catheter in a patient's arm;

FIG. 5 is a perspective view of another embodiment of this invention in a catheter anchor tape;

FIG. 6 is a view taken on line 6—6 of FIG. 5;

FIG. 7 is a view taken on line 7—7 of FIG. 5; and

FIG. 8 is a perspective view showing the installation of the second embodiment of the invention to secure a catheter in a patient's arm.

BEST MODE FOR CARRYING OUT THE INVENTION

Referring now to the drawings there is shown an illustrative embodiment of the invention in an anchor tape for use with an intravenous (IV) catheter. In the illustrative embodiments, each anchor tape is fabricated from pressure sensitive tape as a separate unit for easy accessability; also, each separate anchor tape is provided with removable backing to protect the adhesive during handling. Preferably, the tape is a clear non-allergenic tape of the type which is currently used by emergency medical technicians for making IV catheter anchors. It will be appreciated, as the description proceeds, that the invention is useful in other embodiments and applications.

A first embodiment of the invention is shown in FIGS. 1 through 4. In this embodiment, an anchor tape 10 comprises a unitary strip of pressure sensitive tape 12 which is generally rectangular in shape. It is suitably about five inches long and about one and one-half inches wide. The strip of tape 12 comprises, in general, three interconnected bands. Namely, a first side band 14, an intermediate band 16 and a second side band 18. The intermediate band 16 is joined to the first side band 14 only by a unitary hinge or junction 20 located near the middle or mid-length of the strip, there being slits 22 and 24 in the tape from the ends to the junction 20. Similarly, the second side band 18 of the tape 12 is joined to the intermediate band 16 only by a unitary hinge or junction 26 located near the mid-length of the strip 10, there being slits 28 and 30 from the ends of the tape to the junction 26. The width of the first side band 14 is somewhat greater than the combined widths of the bands 16 and 18.

The first side band 14 of tape 12 has a lower or inner surface 32 which is adapted to be placed against the skin of the patient; it has an upper or outer surface 34 adapted to receive the catheter thereon. The lower surface of the first side band 14 is coated with a layer of adhesive 36 and a removable backing strip 38 is provided thereon to protect the adhesive during handling. The intermediate band 16 of the tape 12 is coated on its upper surface with a layer of adhesive 40 which is covered by a removable backing strip 42. The second side band 18 of the tape 12 is coated on its lower surface with a layer of adhesive 44 and a removable backing strip 46 is disposed over the adhesive 44. For convenience, the backing strips 38, 42 and 46 have respective slits 48, 50 and 52 to facilitate removal from the tape.

The use of the anchor tape 10 for an IV catheter is shown in FIG. 4. The anchor tape 10 is applied after the catheter is installed. A typical procedure is as follows. The catheter typically comprises a tubular part 54 for insertion into the vein in the arm of the patient. The tubular part 54 terminates in a cup or coupling 56, both parts being of plastic material. The insertion of the tubular part 54 is accomplished by use of a metal needle which extends through the tubular part 54. The metal needle has a plastic handle which allows the user to see when blood has been struck. When the needle and the tubular part 54 are properly inserted in the vein, the needle is withdrawn by its handle and is discarded. A flexible tube 58 extends from a bag of IV fluid and terminates in a coupling 60 which is inserted into the coupling 56.

With the catheter installed as described above, the anchor tape 10 is prepared for use by removing the backing strip 38 from the first side band 14 and by removing the backing strip 46 from the second side band 18. The anchor tape is then positioned with the inner surface 32 toward the arm of the patient and is located thereon so that the edge of the second side band 18 is immediately adjacent the point of entry of the tubular part 54 into the arm. In this position, the coupling 56 and coupling 60 are disposed over the unitary junctions 20 and 26 of the anchor tape 10. The first side band 14 and the second side band 18 are pressed against the arm to obtain good adhesion. Next, the backing strip 42 is removed from the intermediate band 16. One free end 62 of the band 16 is wrapped half-way around the coupling 56 and is extended obliquely thereof and pressed into engagement with the patient's arm so that it adheres to the coupling 56 and the arm. Similarly, the free end 64 of the intermediate band 16 is wrapped half-way around the coupling 56 and extends over the other free end obliquely of the coupling member and is pressed against the patient's arm for adhesion thereto. As a result, the coupling 56 and the tubular part 54 are firmly captivated by the intermediate band 16 and the catheter is anchored to the arm against unwanted dislocation.

Another anchor tape 70, according to the second embodiment of the invention, will be described with reference to FIGS. 5 through 8. The anchor tape 70 comprises an adhesive tape 72 which is generally rectangular and is suitably of about the same dimensions as the previously described embodiment. It comprises a first side band 74, an intermediate band 76 and a second side band 78. The first side band 74 is somewhat wider between its free end 80 and the mid-length of the tape than it is between its free end 82 and mid-length of the tape. The intermediate band 76 is joined to the first side band only by a unitary hinge or junction 84, there being slits 86 and 88 extending from the ends of the tape to the junction 84. The intermediate band 76 is somewhat wider between its free end 90 and the mid-length of the tape than it is between its free end 92 and the mid-length of the tape. The second side band 78 is joined to the intermediate band 76 only by a unitary hinge or junction 94 located near the mid-length of the tape, there being slits 96 and 98 extending from the ends of the tape to the junction 94. The side band 78 is the same width between its free end 100 and the mid-length of the tape as it is between its free end 102 and the mid-length of the tape.

The lower or inner surface of the first side band 74 is coated with a layer of adhesive 104 on that part which lies on the right hand side of the dashed line arrow 106 in FIG. 5. A removable backing strip 106 is disposed over the adhesive 104. The outer surface of the second side band 78, the intermediate band 76 and that portion of band 74 lying to the left of dashed line arrow 106 is coated with a layer of adhesive 108. A removable backing 110 is disposed over the adhesive 108.

The use of the anchor tape 70 for an IV catheter is illustrated in FIG. 8. After the catheter is installed, the anchor tape 70 is prepared for use by removing a backing strip 106 and positioning the tape so that the free edge of the side band 78 is immediately adjacent the point of entry of the tubular portion 54. The tape is located laterally so that the mid-length thereof is positioned under the couplings 56 and 60 so that they are opposite the junctions 84 and 94. The adhesive 104 on the side band 74 is pressed against the arm to hold the tape in place. The free end 102 of the side band 78 is wrapped half-way around the coupling 56 and is adhered thereto and to the arm. Similarly, the free end 100 of the side band 78 is wrapped half-way around the coupling 56 and adhered thereto and to the arm. These free ends extend obliquely of the couplings. Next, the free end 92 of the intermediate band 76 is wrapped half-way around the coupling 60 and extended in an oblique direction and adhered to the coupling member and to the arm. As a final step, the free end 90 of the intermediate band 76 is wrapped half-way around the coupling and extended in a direction perpendicular to the coupling. The tube 58 is looped back under the free end 90 which overlaps the side band 74 and which is adhered to the side band 74 and to the arm to hold the tube 58 in place.

Although the description of this invention has been given with reference to a particular embodiment, it is not to be construed in a limiting sense. Many variations and modifications will now occur to those skilled in the art. For a definition of the invention reference is made to the appended claims.

What is claimed is:

1. A pre-cut anchor tape for securing a catheter to the body of a person, said catheter being of the type having a tubular part adapted for entry into the body and terminating in a coupling with a flexible tube extending from the coupling, said anchor tape comprising:

a unitary strip of tape of uniform width having an inner surface adapted to be placed against the body and having an outer surface adapted to receive the catheter thereon, said strip of tape comprising a first side band, a second side band and an intermediate band, said first side band having an adhesive on its inner surface for securing the strip to the body, said intermediate band being separated from the first side and by first and second slits extending from the respective ends thereof toward the middle thereof and being joined to said first side band only by a first unitary hinge located near the mid-length of said strip, said second side band being separated from the intermediate band by third and fourth slits extending from the respective ends thereof toward the middle thereof and being joined to said intermediate band only by a second unitary hinge located near the mid-length of said strip, each of said bands being of uniform width from its respective hinge to either end, said first and second hinges having a length about equal to the diameter of said coupling and being adapted to receive said coupling thereon with said tubular part inserted into said body, said intermediate band having adhesive on one of its outer and inner surfaces, each of the free ends of said intermediate band extending from said hinges being longer than the circumference of said coupling whereby it is adapted to be wrapped half-way around said coupling and adhere thereto and to the body to secure said catheter to the body, said second side band having adhesive on one of its outer and inner surfaces, and each of the free ends of the said second side band being adapted to be adhered to the body to further secure the catheter to the body wherein at least one of said intermediate band and said second side band has adhesive on its outer surface.

2. The invention as defined in claim 1 wherein said second side band has an adhesive on its outer surface whereby the free ends thereof may be wrapped half-way around the coupling and adhered thereto and to the body.

3. The invention as defined in claim 2 wherein the free ends of said intermediate band are of different widths whereby the free ends thereof may be wrapped half-way around said coupling with the narrower free end adhered to the coupling and to the body and with the wider free end overlapping said tube and being adhered to the first side band and the body.

4. The invention as defined in claim 1 wherein said second side band has an adhesive on its inner surface, whereby the free ends of said second side band may be adhered to the body throughout its length.

* * * * *